US010271888B2

United States Patent
Galm et al.

(10) Patent No.: US 10,271,888 B2
(45) Date of Patent: Apr. 30, 2019

(54) HEX SCREWDRIVER HANDLE

(71) Applicant: DePuy Synthes Products, LLC, Raynham, MA (US)

(72) Inventors: Andre Galm, Solothurn (CH); Stephanie Thomas, Solothurn (CH); Eva Lietz, Solothurn (CH); Martin Aeberhard, Solothurn (CN)

(73) Assignee: DePuy Synthes Products, Inc., Raynham, MA (US)

( * ) Notice: Subject to any disclaimer, the term of this patent is extended or adjusted under 35 U.S.C. 154(b) by 360 days.

(21) Appl. No.: 14/320,490

(22) Filed: Jun. 30, 2014

(65) Prior Publication Data
US 2015/0374426 A1    Dec. 31, 2015

(51) Int. Cl.
*A61B 17/88*    (2006.01)
*B25B 15/00*    (2006.01)
*B25B 23/00*    (2006.01)

(52) U.S. Cl.
CPC .......... *A61B 17/8875* (2013.01); *B25B 15/00* (2013.01); *B25B 23/0035* (2013.01)

(58) Field of Classification Search
CPC . B25B 23/0035; B25B 23/0042; B25B 15/00; B25B 15/02; A61B 17/8875
USPC .................................................. 81/438, 490
See application file for complete search history.

(56) References Cited

U.S. PATENT DOCUMENTS

| 1,064,206 | A | * | 6/1913 | Gould | ................. B25B 23/0042 |
| | | | | | 279/104 |
| 4,287,923 | A | | 9/1981 | Hornung | |
| 5,265,504 | A | * | 11/1993 | Fruhm | ................. B25G 1/085 |
| | | | | | 81/177.4 |
| 5,996,452 | A | | 12/1999 | Chiang | |
| 6,951,156 | B2 | * | 10/2005 | Garg | ...................... B25B 13/06 |
| | | | | | 81/121.1 |
| 6,968,760 | B2 | * | 11/2005 | Hu | ........................ B25G 1/085 |
| | | | | | 81/439 |
| 7,146,885 | B2 | | 12/2006 | Hwang et al. | |

(Continued)

FOREIGN PATENT DOCUMENTS

| CN | 1501791 | 6/2004 |
| CN | 1849200 | 10/2006 |

(Continued)

*Primary Examiner* — Hadi Shakeri
(74) *Attorney, Agent, or Firm* — Fay Kaplun & Marcin, LLP

(57) ABSTRACT

A screwdriver includes a handle having a handle channel extending therethrough and a shaft extending from a proximal end insertable into the handle channel to a distal end including a bit opening sized to receive a proximal portion of a bit therein in combination with a locking sleeve slidably receiving the shaft therethrough and positionable over the shaft distally of the handle and a spring slidably received within the locking sleeve channel over the shaft. A coupling member received over the shaft distally of the locking sleeve is movable from a biased first configuration in which a locking element protrudes radially into the bit opening to lockingly engage a bit received therein and a second configuration in which the coupling member is retracted proximally to compress the spring and permit the locking element to move radially out of the bit opening to permit the bit to be removed therefrom.

15 Claims, 6 Drawing Sheets

(56) References Cited

U.S. PATENT DOCUMENTS

| | | | |
|---|---|---|---|
| 8,505,418 B1 * | 8/2013 | Chiang | B25B 23/0021 81/124.2 |
| 8,876,121 B2 * | 11/2014 | Hu | B25B 23/0035 279/143 |
| 2008/0243133 A1 * | 10/2008 | Heinz | B25B 23/101 606/104 |
| 2013/0096568 A1 | 4/2013 | Justis | |

FOREIGN PATENT DOCUMENTS

| | | |
|---|---|---|
| CN | 203210289 U | 9/2013 |
| EP | 1284122 | 2/2003 |
| EP | 1514645 | 3/2005 |
| EP | 1637285 A1 | 3/2006 |
| EP | 2623059 | 8/2013 |
| TW | M 251697 | 12/2004 |
| TW | M 338723 | 8/2008 |

\* cited by examiner

HEX SCREWDRIVER HANDLE

FIELD OF THE INVENTION

The present invention generally relates to a screwdriver handle for use in the fixation of fractures of the hand and methods of using the screwdriver handle.

BACKGROUND

Procedures for the fixation of fractured or otherwise damaged bone often require the use of a driving device such as a screwdriver to drive a bone screw through a bone plate and into a bone. In some procedures, a plurality of screwdrivers must be used, with each screwdriver including a differently sized bit to engage a different size of screw. In other procedures, a single screwdriver is provided and a selected one of a plurality of bits is coupled thereto to accommodate differently sized screws. However, the procedure for coupling each of the bits to the handle may be cumbersome. Furthermore, certain removably coupleable bits have been prone to dislodging from the handle during procedures.

SUMMARY OF THE INVENTION

The present invention is directed to a screwdriver comprising a handle extending from a proximal end to a distal end and having a handle channel extending therethrough and a shaft extending from a proximal end insertable into the handle channel to a distal end, the distal end of the shaft including a screw bit opening sized to receive a proximal portion of a screw bit therein in combination with a locking sleeve having a locking sleeve channel slidable receiving the shaft therethrough, the locking sleeve being positionable over the shaft distally of the handle and a spring slidably received within the locking sleeve channel and over the shaft. A coupling member received over the shaft distally of the locking sleeve is movable from a biased first configuration in which a locking element protrudes radially into the bit opening to lockingly engage a bit received therein and a second configuration in which the coupling member is retracted proximally to compress the spring and permit the locking element to move radially out of the bit opening to permit the bit to be removed therefrom, wherein the handle, shaft, locking sleeve, spring and coupling member are removably attached to one another.

BRIEF DESCRIPTION OF THE DRAWINGS

Several embodiments of the invention will be described in the following by way of example and with reference to the accompanying drawings in which.

DETAILED DESCRIPTION

Figure 1:
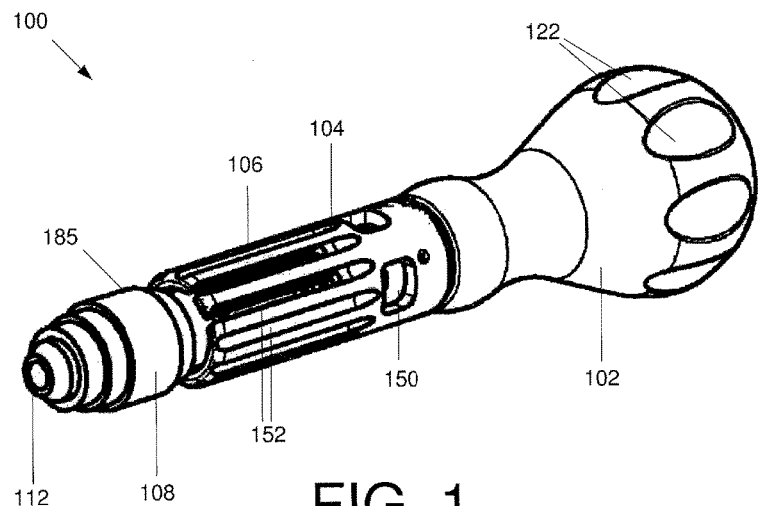
FIG. 1 shows a perspective view of a screwdriver according to an exemplary embodiment of the invention.
Figure 2:
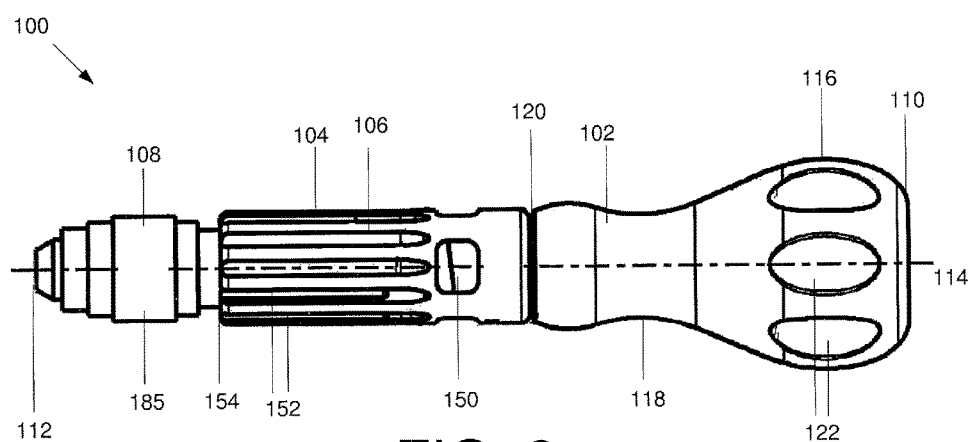
FIG. 2 shows a side view of the screwdriver of FIG. 1.

The exemplary embodiments may be further understood with reference to the following description and the appended drawings, wherein like elements are referred to with the same reference numerals. The exemplary embodiments relate to a screwdriver including a plurality of components which are easily removable and attachable to one another to aid in cleaning and sterilization thereof between procedures. Specifically, the screwdriver comprises a handle portion and an elongated shaft portion removably attachable thereto, a distal end of the shaft portion having a bit opening removably engaging a bit. An outer sleeve is slidably received over the shaft distally of the handle. Finally, a coupling member is received over the shaft distally of the sleeve. A locking mechanism is provided on the shaft and is movable from a first configuration in which a protruding portion thereof extends into the bit opening and a second configuration in which the protruding portion is permitted to move radially outward to leave the bit opening unobstructed. In an operative configuration, the coupling member is moved proximally while maintaining the handle stationary, the proximal movement compressing a spring housed within the sleeve. The proximal movement of the coupling releasing a compressive force applied on the protruding portion and moving the locking mechanism to the second configuration. A bit may then be inserted into the bit channel. A subsequent release of the proximal force applied to the coupling member permits the coupling member to move distally due to an axially expansive force applied thereto by the spring. Distal movement of the coupling member moves the locking member to the first configuration to lock the protruding portion in a corresponding opening formed in a proximal end of the bit, thereby locking the bit to the screwdriver.

Figure 3:
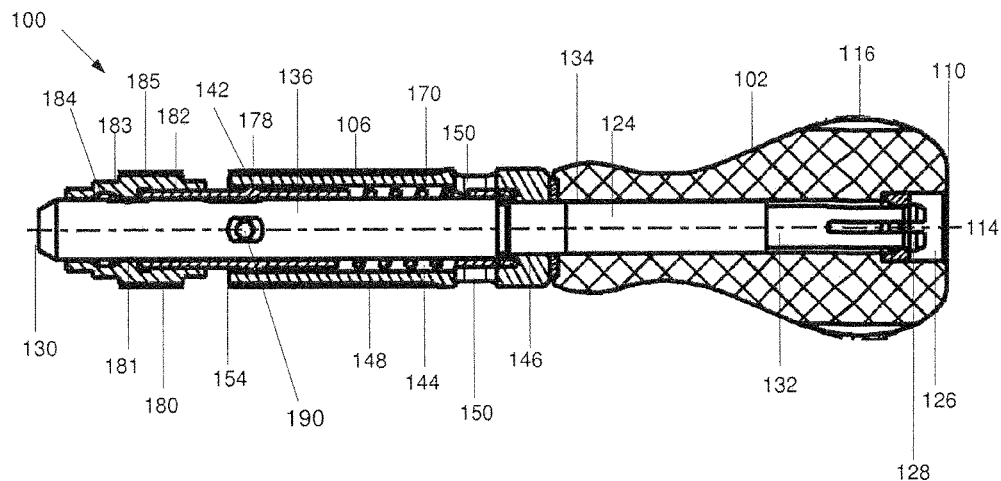
FIG. 3 shows a cross-section view of the screwdriver of FIG. 1.
Figure 4:
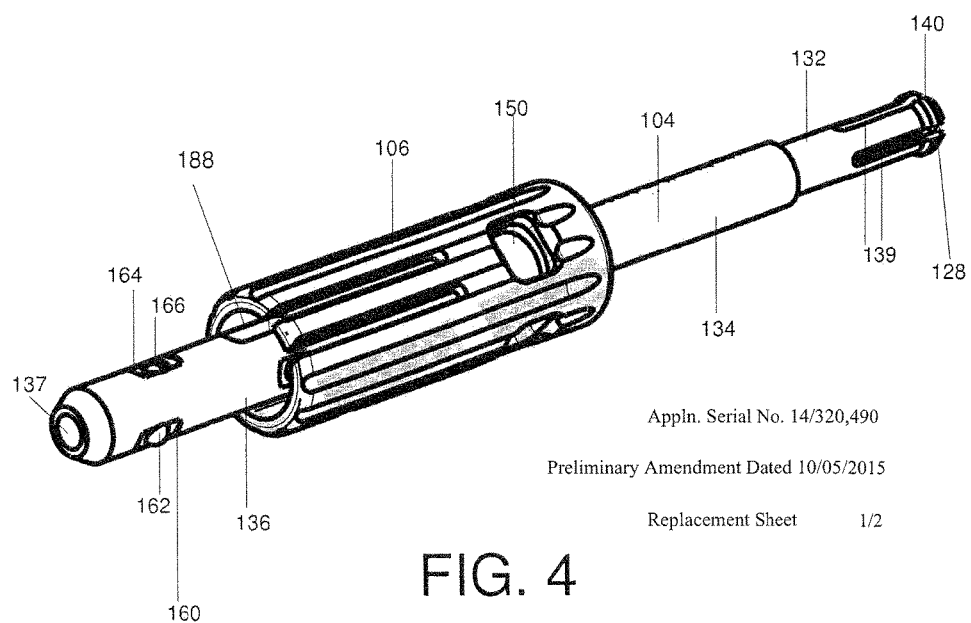
FIG. 4 shows a perspective view of a shaft and sleeve of the screwdriver of FIG. 1.

As shown in FIGS. 1-11, a screwdriver 100 according to the present invention comprises a handle 102, a shaft 104, a sleeve 106 and a coupling member 180. The screwdriver extends from a proximal end 110 of the handle 102 to a distal end 112 of the hex coupling 180 along a central longitudinal axis 114. The handle 102 is formed with a bulb shape. Specifically, the handle 102 increases from a first diameter at the proximal end 110 to a maximum diameter at a bulbous portion 116 and includes a tapered portion 118 adjacent a distal end 120 thereof, the tapered portion 118 being formed to aid in ergonomic handling thereof, as those skilled in the art will understand. The handle 102 includes a plurality of axial cutouts 122 at the bulbous portion 116 extending parallel to the longitudinal axis 114. The cutouts 122 are configured to enhance a grip by a user thereon, as those skilled in the art will understand. Furthermore, the cutouts 122 prevent the screwdriver 100 from rolling when seated on an operating table or other surface. As shown in FIG. 3, a channel 124 extends through the handle 102 in alignment with the central longitudinal axis 114. The channel 124 has an enlarged diameter region 126 at a proximal end thereof, which is open to the proximal end 110 of the handle 102. As will be described in greater detail later on, the channel 124 is sized and shaped to receive a portion of the shaft 104 therethrough.

As shown in FIGS. 3-6, the shaft 104 extends from a proximal end 128 to a distal end 130. The shaft 104 includes first, second and third elongated cylindrical portions 132, 134, 136 with a first outer diameter of the first portion 132 being smaller than a second outer diameter of the second portion 134, while the second outer diameter is smaller than a third outer diameter of the third portion 136. The first portion 132 is sized to permit slidable insertion thereof into and out of the channel 124 of the handle 102. The third portion 136 is sized to permit insertion thereof into a channel 144 extending through the sleeve 106 by only a predetermined depth, as will be described in greater detail later on. A channel 137 extends proximally into the third element 136 from the distal end 130, the channel 137 being sized to receive a bit (not shown) in an operative configuration.

The first portion 132 also includes a plurality of axially extending slots 139 open to the proximal end 128 and extending parallel to the longitudinal axis 114. The proximal end 128 further comprises an increased diameter portion 140 having an outer diameter equal to or greater than a diameter of the channel 124. In order to assemble the screwdriver 100, the proximal end 128 of the first element 132 is inserted into the channel 124. As the shaft 104 is slid through the channel 124, the increased diameter portion 140 is compressed radially inward by the walls of the channel 124. When moved into the enlarged diameter region 126 of the channel 124, the increased diameter portion 140 expands under its natural bias back to its expanded configuration, locking the shaft 104 in the handle 102.

The third portion 136 of the shaft 104 further comprises a first milled portion 160 along an exterior thereof for housing a first ball 162 therein. The first milled portion 160 may be configured as a slot elongated in a direction extending along the axis 114, the slot sized and shaped to prevent the first ball 162 from becoming disengaged from the third portion 136 of the shaft 104. In an operative configuration, the first ball 162 removably engages a groove (not shown) formed on an inner wall of a channel 181 extending through the coupling 180, as will be described in greater detail with respect to the exemplary method. This groove may extend about a circumference of the inner wall of the channel 181 so that the coupling 180 may engage the first ball 162 in any orientation with respect to the shaft 104. Specifically, the ball 162 is biased (e.g., by a spring (not shown)) to project out of the first milled portion 160 a predetermined distance. In an operative configuration, as the third portion 136 is pushed into the sleeve 106, walls of the channel 144 push the ball 162 radially into the first milled portion 160 until the first milled portion 160 is axially aligned with the groove (not shown). At this point, the ball 162 is moves radially outward (through the action of the spring (not shown)) to lock the shaft 104 to the coupling 180. It is noted that the present disclosure is directed to a ball, an alternate embodiment may include a retractable protrusion having any other size and/or shape.

The third portion 136 also comprises a second milled portion 164 housing a second ball 166 therein. The second milled portion 164 may be configured as a slotted opening extending laterally through a wall of the third portion, the opening sized and shaped to prevent the second ball 166 from becoming disengaged from the shaft 104. In a preferred embodiment, the second milled portion 164 is offset from the first slot 160 by 90 degrees, although any other orientation is envisioned within the scope of the disclosure. The second ball 166 is also offset from the first ball 162 along a length of the shaft 104 such that, when the first ball 162 is received within the circumferential groove along the inner wall of the channel 181, the second ball 166 engages a non-grooved portion of the inner wall 181, forcing the second ball 166 radially inward into the channel 137. Thus, the second milled portion 164 is open to the channel 137 and the second ball 166 is operable (e.g., under bias of a spring (not shown)) to lockingly engage a circumferential groove (not shown) formed in a proximal end of a bit (not shown) that is received within the channel 137.

Figure 5:
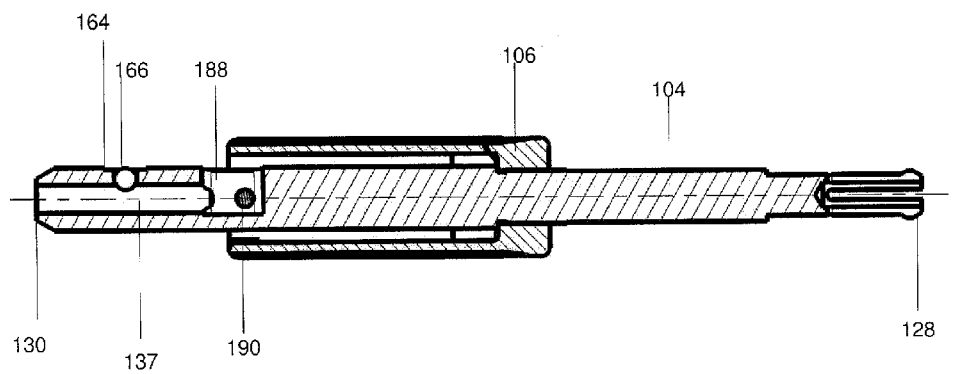
FIG. 5 shows a cross-section view of the shaft and sleeve of FIG. 4.
Figure 6:
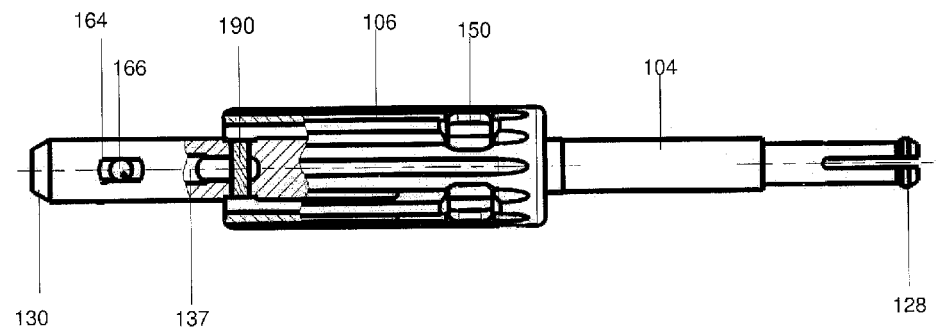
FIG. 6 shows a partial cross-section view of the shaft and sleeve of FIG. 4.
Figure 7:
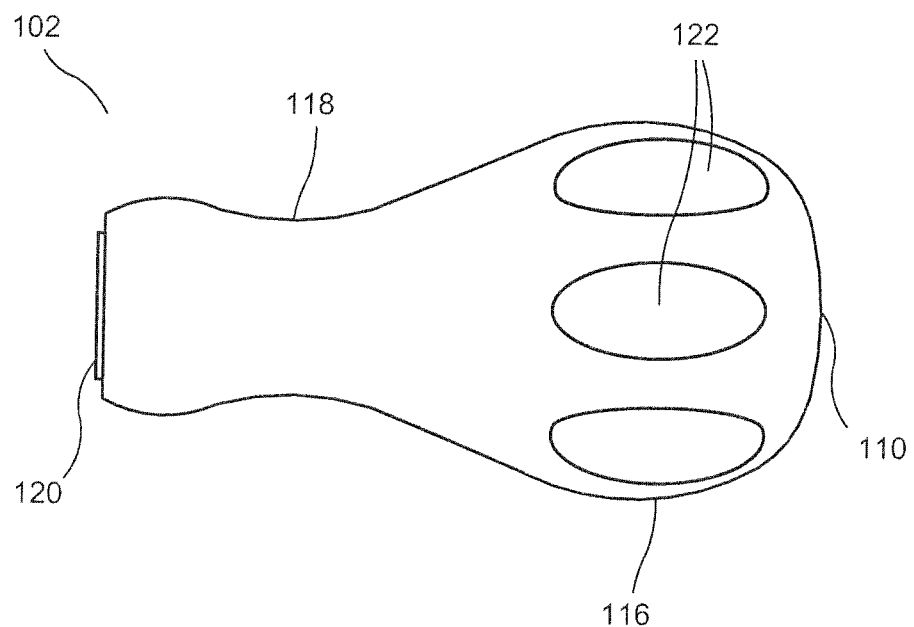
FIG. 7 shows a side view of a handle of the screwdriver of FIG. 1.
Figure 8:
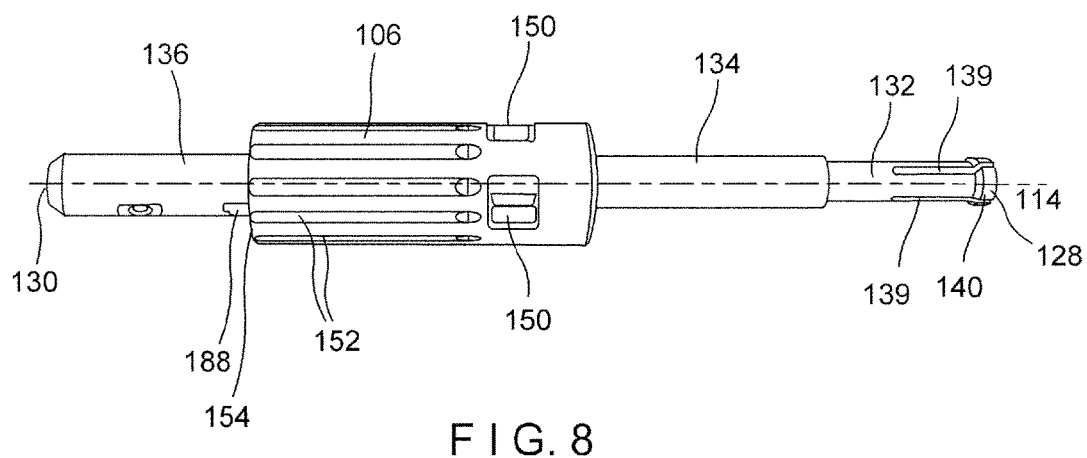
FIG. 8 shows a side view of the shaft and sleeve of FIG. 4.

Proximally of the first and second balls 162, 166, the third portion 136 may also comprise a window 188 extending laterally through a wall thereof. The window 188 may be open to, for example, a proximal end of the channel 137 to provide ease of cleaning thereof. The third portion 136 may also comprise a proximal stop 190 positioned within the channel 137 of the shaft 104 to prevent a bit engaged thereto from extending proximally therepast. The stop 190 may be configured as a pin extending substantially perpendicularly through the channel 137 of the third portion 136 of the shaft 104 to prevent the bit from being moved proximally therebeyond. As shown in FIGS. 5 and 6, the stop 190 may be substantially axially aligned with the window 188.

As shown in greater detail in the cross-sectional view of FIG. 3, the channel 144 includes a first channel portion 146 sized to receive the second portion 134 therethrough while preventing the third portion 136 entering therein. The channel 144 also includes a second channel portion 148 having a diameter larger than that of the first channel portion 146. The second channel portion is sized to receive a spring 170 therein, as will be described in greater detail later on. A plurality of openings 150 extending through a proximal portion of the sleeve 106 are open to the sleeve channel 144. The openings 150 are rectangular with rounded corners, although other shapes (e.g., circular, triangular, etc.) are envisioned within the scope of the invention. The openings 150 are aligned with one another along a length of the sleeve 106 in a plane orthogonal to the central longitudinal axis 114. The openings 150 aid in cleaning of the screwdriver 100 between medical procedures, as those skilled in the art will understand. Specifically, the openings 150 permit the flow of water or other cleaning agents therethrough while also preventing the accumulation of bacteria, tissue, blood, as is common with screwdrivers having a closed shape. Furthermore, the openings 150 are configured to enable laser welding of the sleeve 106 to the shaft 104. In a preferred embodiment, the screwdriver 150 include four openings 150 distributed evenly about a circumference thereof. It is noted, however, that this number and spatial arrangement of the openings 150 is exemplary only and that any of one, two, three, four, five or more openings 150 may be employed in any desired spacing without deviating from the scope of the invention. A plurality of cutouts 152 is formed in an outer surface of the sleeve 106 with the cutouts 152 distributed over an outer surface thereof distally of the openings 150 and extending parallel to the axis 114. The cutouts 152 extend into the sleeve 106 by a distance less than a thickness of the sleeve 106 to define reduced thickness portions of the sleeve 106 and are open to a distal end 154 of the sleeve 106. Similar to the cutouts 122, the cutouts 152 aid in gripping of the sleeve 106 and aid in preventing the screwdriver 100 from rolling when seated on an operating table or other surface.

Figure 9:
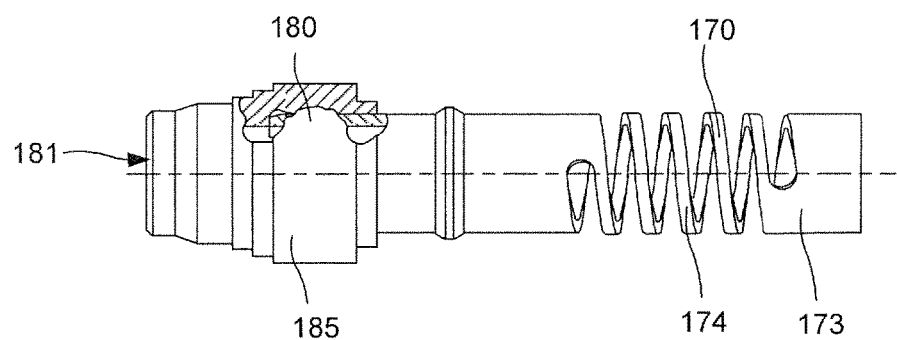
FIG. 9 shows a partial cross-sectional side view of a spring and coupling member of the screwdriver of FIG. 1.
Figure 10:
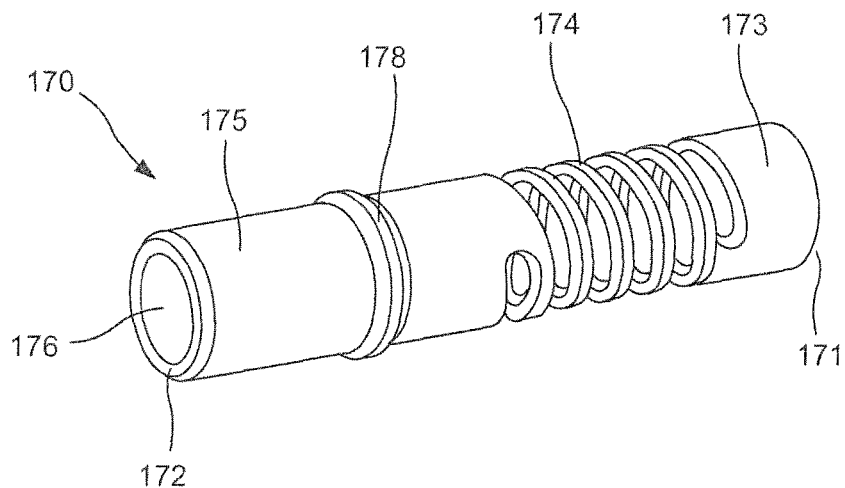
FIG. 10 shows a perspective view of the spring of FIG. 9.
Figure 11:
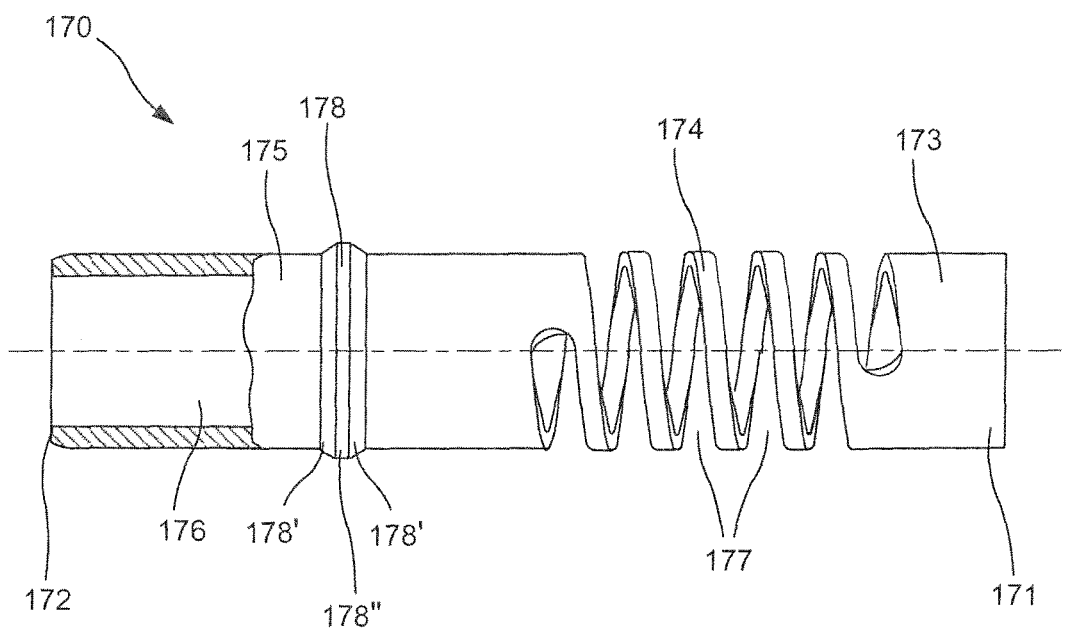
FIG. 11 shows a partial cross-sectional view of the spring of FIG. 9.

As shown in FIGS. 9-11, the spring 170 is formed as an elongated cylindrical element extending from a proximal end 171 to a distal end 172 and includes a channel 176 extending therethrough. The spring 170 includes a first cylindrical portion 173, a coiled portion 174 and a second cylindrical portion 175. The first cylindrical portion 173 in this embodiment is 6 mm in length, although other measurements may be used without deviating from the scope of the invention. The coiled portion 174 according to this embodiment includes four or five turns and has a pitch of 3 mm. The coiled portion 174 may be defined by one or more elongated helical cutouts 177 extending through a body of the spring 170. The second cylindrical portion 175 includes a radial abutment 178 projecting radially outward therefrom defining an increased diameter portion of the spring 170. The radial abutment 178 may be formed of first and second angled walls 178' converging to a common third wall 178", with the first and second walls 178' of this embodiment forming an angle of 30° with an outer body of the spring 170. In an operative configuration, the radial abutment 178 engages a groove 142 formed on a wall of the channel 144 of the sleeve 106 to lock a position of the spring 170 relative thereto.

As shown in FIGS. 3 and 9, the coupling member 180 is formed as an elongated element having a channel 181 extending therethrough. A first portion 182 of the channel 181 is sized to receive the second cylindrical portion 175 of the spring 170 while a second portion 183 of the channel 181 is sized to prevent the spring 170 from entering therein. The second portion 183 includes a recess 184 defining an increased diameter portion of the channel 181 and is sized to lockingly engage the ball 166 in an operative configuration. In an operative configuration, a user grips an outer surface 185 of the coupling 180 and pulls the coupling 180 proximally toward the handle 102. This movement compresses the spring 170 and moves outer wall 185 proximally so that the ball 166 is exposed. This movement permits the second ball 166 to spring radially outward to a biased configuration in which the channel 137 is unobstructed and a bit (not shown) is slidably received therein. Releasing the proximally directed pressure on the outer surface 185 permits the coupling 180 to move distally and force the ball 166 radially inward to extend into the channel 137, thereby lockingly engaging the circumferential groove (not shown) formed at the proximal end of the bit. As the coupling 180 moves distally to force the second ball 166 into engagement with the bit received within the channel 137, the coupling 180 simultaneously receives the first ball 162 within the groove thereof to lock the coupling 180 relative to the shaft 104, preventing the bit from becoming inadvertently dislodged therefrom.

In accordance with an exemplary method according to the invention, the shaft 104 is inserted into the distal end 154 of the sleeve 106 and into the handle 102 until the increased diameter portion 140 lockingly engages the enlarged diameter region 126 of the channel 124. The hex coupling 180 is then fitted with the spring 170 and slidably inserted into the channel 144 of the sleeve 106 until (1) the radial abutment 178 lockingly engages the recess 142, (2) the first ball 162 lockingly engages a groove (not shown) formed in the channel 181 of the coupling 180 and (3) the second ball 166 engages a non-grooved portion of the channel 181. In this assembled configuration, the surgeon or other user may retract the coupling 180 in a proximal direction while maintaining the handle 102 in a stationary position, the retraction causing an axial compression of the spring 170 and opening the channel 137 to permit insertion of a bit therein. In particular, moving the coupling 180 proximally relative to the shaft 104 causes the second ball to spring radially outward, out of the channel 137 to permit a proximal portion of a bit to be received therein. Release of the coupling 180 permits the spring 170 to return to a biased axially expanded configuration, moving the coupling 180 distally to lockingly engage the bit, as described in greater detail earlier.

It will be appreciated by those skilled in the art that various modifications and alterations of the disclosed embodiments may be made without departing from the broad scope of the invention. Some of these have been discussed above and others will be apparent to those skilled in the art.

What is claimed is:

1. A screwdriver, comprising:
a handle extending from a proximal end to a distal end and having a handle channel extending therethrough;
a shaft extending from a proximal end insertable into the handle channel to a distal end, the distal end of the shaft including a bit opening sized to receive a proximal portion of a bit therein;
a locking sleeve coupled to and in contact with the shaft, the locking sleeve having a locking sleeve channel slidably receiving the shaft therethrough, the locking sleeve being positionable over the shaft distally of the handle;
a spring slidably received within the locking sleeve channel and over the shaft; and
a coupling member received over the shaft, so that the entire coupling member extends distally of the locking sleeve, the coupling member being movable from a biased first configuration in which a locking element protrudes radially into the bit opening to lockingly engage, distally of the locking sleeve, a bit received therein and a second configuration in which the coupling member is retracted proximally to compress the spring and permit the locking element to move radially out of the bit opening to permit the bit to be removed therefrom;
wherein the handle, shaft, locking sleeve, spring and coupling member are removably attached to one another.

2. The screwdriver of claim 1, wherein the locking sleeve includes a plurality of openings extending therethrough to aid in sterilization thereof.

3. The screwdriver of claim 1, wherein an outer wall of the locking sleeve includes a plurality of axial slots formed to prevent the locking sleeve from rolling when seated on a surface.

4. The screwdriver of claim 1, wherein the locking element is received within a first slotted opening formed in the shaft.

5. The screwdriver of claim 4, wherein the locking element is a first ball bearing.

6. The screwdriver of claim 1, wherein an outer wall of the handle includes a plurality of axial slots formed to prevent the locking sleeve from rolling when seated on a surface.

7. The screwdriver of claim 1, wherein a proximal end of the shaft includes a radial abutment sized to lockingly engage a corresponding enlargement formed in the handle channel.

8. The screwdriver of claim 1, further comprising a window extending laterally through a portion of the shaft, the window being open to the bit opening to aid in cleaning and sterilization thereof.

9. The screwdriver of claim 1, further comprising a stop extending transversely through the bit opening to prevent a bit received within the bit opening from being moved proximally therepast.

10. The screwdriver of claim 9, wherein the stop is a pin extending substantially perpendicularly through the bit opening.

11. A screwdriver, comprising:
a handle extending from a proximal end to a distal end and having a handle channel extending therethrough;
a shaft extending from a proximal end insertable into the handle channel to a distal end, the distal end of the shaft including a bit opening sized to receive a proximal portion of a bit therein;
a locking sleeve having a locking sleeve channel slidably receiving the shaft therethrough, the locking sleeve being positionable over the shaft distally of the handle;
a spring slidably received within the locking sleeve channel and over the shaft, wherein the spring includes a helical member bounded on proximal and distal ends by proximal and distal elongated cylindrical members; and
a coupling member received over the shaft distally of the locking sleeve, the coupling member being movable from a biased first configuration in which a locking element protrudes radially into the bit opening to lockingly engage a bit received therein and a second configuration in which the coupling member is retracted proximally to compress the spring and permit the locking element to move radially out of the bit opening to permit the bit to be removed therefrom;
wherein the handle, shaft, locking sleeve, spring and coupling member are removably attached to one another.

12. The screwdriver of claim 11, wherein the distal elongated cylindrical member includes a radial abutment formed to lockingly engage a corresponding recess formed on a wall of the locking sleeve channel;
wherein the locking element is received within a first slotted opening formed in the shaft; and
wherein the locking element is a first ball bearing.

13. A screwdriver, comprising:
a handle extending from a proximal end to a distal end and having a handle channel extending therethrough;
a shaft extending from a proximal end insertable into the handle channel to a distal end, the distal end of the shaft including a bit opening sized to receive a proximal portion of a bit therein;
a locking sleeve having a locking sleeve channel slidably receiving the shaft therethrough, the locking sleeve being positionable over the shaft distally of the handle;
a spring slidably received within the locking sleeve channel and over the shaft;
a coupling member received over the shaft distally of the locking sleeve, the coupling member being movable from a biased first configuration in which a locking element protrudes radially into the bit opening to lockingly engage a bit received therein and a second configuration in which the coupling member is retracted proximally to compress the spring and permit the locking element to move radially out of the bit opening to permit the bit to be removed therefrom, wherein the locking element is a first ball bearing and is received within a first slotted opening formed in the shaft; and
a second slotted opening formed in the shaft distally of the first slotted opening and receiving a second ball bearing therein, the second ball bearing being formed to removably lockingly engage a wall of a coupling channel extending through the coupling member,
wherein the handle, shaft, locking sleeve, spring and coupling member are removably attached to one another.

14. The screwdriver of claim 13, wherein, when the coupling channel lockingly engages the second ball bearing, the first ball bearing is forced radially into the bit opening.

15. A screwdriver, comprising:
a handle extending from a proximal end to a distal end and having a handle channel extending therethrough;
a shaft extending from a proximal end received into the handle channel to a distal end, the distal end of the shaft including a bit opening sized to receive a proximal portion of a bit therein;
a locking sleeve coupled to and in contact with the shaft, the locking sleeve having a locking sleeve channel slidably so that the locking sleeve is mounted over the shaft distally of the handle;
a spring slidably mounted between the locking sleeve channel and the shaft; and
a coupling member received over the shaft, so that the entire coupling member extends distally of the locking sleeve, the coupling member being movable from a biased first configuration in which a locking element protrudes radially into the bit opening, distally of the locking sleeve and a second configuration in which the coupling member is retracted proximally to compress the spring and permit the locking element to move radially out of the bit opening.

* * * * *